US008431358B2

(12) United States Patent
Sadowski et al.

(10) Patent No.: US 8,431,358 B2
(45) Date of Patent: Apr. 30, 2013

(54) METHOD FOR PROCESSING COALESCENCE-INHIBITED EMULSIONS FROM WHOLE-CELL BIOTRANSFORMATIONS WITH COMPRESSED OR SUPERCRITICAL GASES

(75) Inventors: Gabriele Sadowski, Dortmund (DE); Andreas Schmid, Dortmund (DE); Bruno Buehler, Dortmund (DE); Michael Goernert, Dortmund (DE); Christoph Brandenbusch, Essen (DE)

(73) Assignee: Technische Universitaet Dortmund, Dortmund (DE)

( * ) Notice: Subject to any disclaimer, the term of this patent is extended or adjusted under 35 U.S.C. 154(b) by 287 days.

(21) Appl. No.: 12/452,769

(22) PCT Filed: Jul. 20, 2008

(86) PCT No.: PCT/DE2008/001177
§ 371 (c)(1),
(2), (4) Date: Feb. 16, 2010

(87) PCT Pub. No.: WO2009/012754
PCT Pub. Date: Jan. 29, 2009

(65) Prior Publication Data
US 2010/0145082 A1    Jun. 10, 2010

(30) Foreign Application Priority Data

Jul. 21, 2007  (DE) .......................... 10 2007 034 258
Dec. 6, 2007   (DE) .......................... 10 2007 059 389

(51) Int. Cl.
*C12P 1/00* (2006.01)
(52) U.S. Cl.
USPC ............. 435/41; 435/171; 435/170; 435/169; 516/133; 516/197
(58) Field of Classification Search .................... 435/41, 435/170, 171, 169; 516/133, 197
See application file for complete search history.

(56) References Cited

U.S. PATENT DOCUMENTS

| 6,413,430 | B1 | 7/2002 | Berger |
| 6,566,410 | B1 | 5/2003 | Zaki et al. |
| 2005/0077241 | A1* | 4/2005 | Alkhalidl ....................... 210/634 |
| 2010/0004382 | A1* | 1/2010 | Varadaraj et al. ............. 524/577 |

FOREIGN PATENT DOCUMENTS

| DE | 40 28 904 | 7/1992 |
| DE | 197 54 756 | 4/1999 |
| DE | 199 26 577 | 12/2000 |
| DE | 101 14 920 | 10/2002 |
| EP | 0 404 370 | 12/1990 |
| EP | 0 492 857 | 7/1992 |
| WO | WO 99/00352 | 1/1999 |
| WO | WO 01/46353 | 6/2001 |

OTHER PUBLICATIONS

Definition of emulsion downloaded from http://medical-dictionary.thefreedictionary.com/emulsion on Jan. 14, 2012.*
R. León, P. Fernandes, H. M. Pinheiro, and J, M. S. Cabral, "Whole-cell biocatalysis in organic media," *Enzyme and Microbial Technology*, vol. 23, pp. 483-500, Dec. 15, 1998. (Spec, p. 30).
M. D. Lilly, "Two-liquid-phase biocatalytic reactions," *Journal of Chemical Technology and Biotechnology*, vol. 32, pp. 162-169, 1982. (Spec, p. 30).
P. Nikolova and O. P. Ward, "Whole cell biocatalysis in nonconventional media," *Journal of Industrial Microbiology*, vol. 12, pp. 76-86, 1993. (Spec, p. 30).
G. J. Salter and D. B. Kell, "Solvent Selection for Whole Cell Biotransformations in Organic Media," *Critical Reviews in Biotechnology*, vol. 15, pp. 139-177, 1995. (Spec, p. 30).
B. Bühler and A. Schmid, "Process implementation aspects for biocatalytic hydrocarbon oxyfunctionalization," *Journal of Biotechnology*, vol. 113, pp. 183-210, Sep. 30, 2004. (Spec, p. 30).
H. M. Van Sonsbeek, H. H. Beeftink, and J. Tramper, "Two-liquid-phase bioreactors," *Enzyme and Microbial Technology*, vol. 15, pp. 722-729, Sep. 1993. (Spec, p. 30).
S.-D. Yeo and A. Akgerman, "Supercritical Extraction of Organic Mixtures from Aqueous-Solutions," *AIChE Journal*, vol. 36, No. 11, pp. 1743-1747, Nov. 1990. (Spec, p. 30).
N. N. Zaki, R. G. Carbonell, and P. K Kilpatrick, "A Novel Process for Demulsification of Water-in-Crude Oil Emulsions by Dense Carbon Dioxide," *Industrial & Engineering Chemistry Research*, vol. 42, pp. 6661-6672, Dec. 10, 2003. (Spec, p. 30).
International Search Report, mailed May 3, 2009.
A. Kollmer, Verfahrenstechnische Aspekte bei zweiphasigen Bioprozessen, in *Institute of Biotechnolgy* Zurich: Swiss Federal Institute of Technology, 1997., p. 1-202.
R. G. Mathys, "Bioconversion in two-liquid phase systems: downstream processing," in *Institute of Biotechnolgy* Zurich: Swiss Federal Institute of Technology, pp. 33-37 and 100-111, 1997.
A. Schmid, "Two-liquid Phase Bioprocess Development. Interfacial Mass Transfer Rates and Explosion Safety," in *Institute of Biotechnolgy* Zurich: Swiss Federal Institute of Technology, pp. 123-129, 1997.
Brandenbusch et al., "Efficient Phase Separation and Product Recovery in Organic-Aqueous Bioprocessing Using Supercritical Carbon Dioxide", in *Biotechnology and Bioengineering*, published online Jun. 2010 at www.interscience.wiley.com, pp. 1-10.

* cited by examiner

*Primary Examiner* — Susan Hanley
(74) *Attorney, Agent, or Firm* — Collard & Roe, P.C.

(57) ABSTRACT

The method separates emulsions derived from whole-cell biotransformations, including stable emulsions derived from typical biocatalytic two-phase processes that result with such a biotransformation. A supercritical extraction to obtain the valuable product can follow directly, because of the use of compressed or supercritical gas as the separation agent. It is unimportant whether the valuable product is present in the aqueous or the organic phase. Recycling of the organic phase is possible, since the surfactant cell components decisively responsible for the formation of the stable emulsion can be separated off via sedimentation, because of the treatment. The achieved separation remains in existence even after the gas has gassed out, so that aside from extraction, other methods for product isolation can also follow, if necessary.

23 Claims, 9 Drawing Sheets

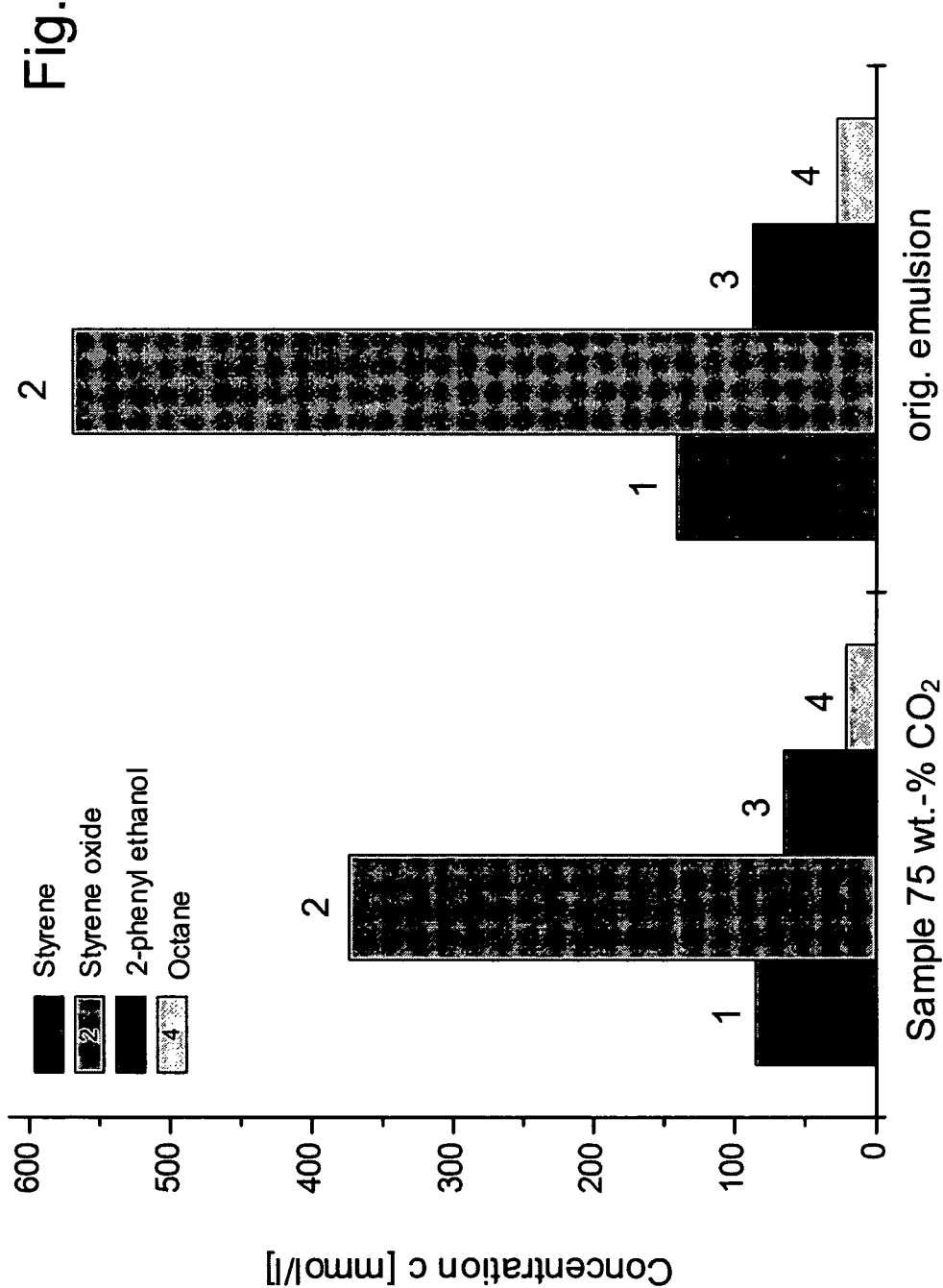

PRIOR ART

| Substance | TC [K] | PC [Mpa] | Substance | TC [K] | PC [Mpa] |
|---|---|---|---|---|---|
| Helium | 5,19 | 0,23 | Propane | 369,8 | 4,25 |
| Hydrogen | 33,0 | 1,29 | Hydrogen sulfide | 373,3 | 8,94 |
| Neon | 44,4 | 2,76 | Ethyl fluoride | 375,3 | 5,02 |
| Nitrogen | 126,2 | 3,39 | Radon | 377,6 | 6,28 |
| Carbon monoxide | 132,9 | 3,50 | Carbonyl sulfide | 378,8 | 6,35 |
| Argon | 150,75 | 4,87 | Dichlorodifluoromethane | 385,0 | 4,14 |
| Oxygen | 154,6 | 5,04 | Perfluorobutane | 386,3 | 2,32 |
| Nitrogen monoxide | 180,15 | 6,48 | Propadiene | 393,1 | 5,47 |
| Methane | 190,4 | 4,60 | Cyclopropane | 397,8 | 5,49 |
| Krypton | 209,45 | 5,50 | Dimethyl ether | 400,0 | 5,24 |
| Trifluorocarbon | 227,6 | 3,74 | Ammonia | 405,5 | 11,35 |
| Trifluorosilicon | 259,1 | 3,72 | Isobutane | 408,2 | 3,65 |
| Silane (SiH$_4$) | 269,69 | 4,84 | Methyl chloride | 416,2 | 6,70 |
| Ethylene | 282,4 | 5,04 | Chlorine | 416,9 | 7,98 |
| Xenon | 289,7 | 5,84 | Hydrogen iodide | 424,0 | 8,31 |
| Hexafluoroethane | 293,0 | 3,06 | n-Butane | 425,0 | 3,80 |
| Trifluoromethane | 299,3 | 4,86 | Methylamine | 430,0 | 7,43 |
| Chlorotrifluoromethane | 301,95 | 3,87 | Sulfur dioxide | 430,8 | 7,88 |
| 1,1-Difluoroethane | 302,85 | 4,46 | Diethyl ether | 466,7 | 3,64 |
| Carbon dioxide | 304,15 | 7,38 | n-Pentane | 469,7 | 3,37 |
| Ethane | 305,4 | 4,88 | Diethyl amine | 496,5 | 3,71 |
| Chlorotrifluorosilane | 307,65 | 3,47 | n-Hexane | 507,5 | 3,01 |
| Acetylene | 308,3 | 6,14 | Acetone | 508,1 | 4,70 |
| Nitrogen dioxide | 309,65 | 7,24 | Isopropanol | 508,3 | 4,76 |
| Monofluoromethane | 315,0 | 5,60 | Methanol | 512,6 | 8,09 |
| Sulfur hexafluoride | 318,75 | 3,76 | Ethanol | 513,9 | 6,14 |
| Hydrochloric acid | 324,7 | 8,31 | Ethyl acetate | 523,2 | 3,83 |
| Trifluorobromomethane | 340,2 | 3,97 | n-Heptane | 540,3 | 2,74 |
| 1,1,1-Trifluoroethane | 346,25 | 3,76 | Acetonitrile | 545,5 | 4,83 |
| Chloropentafluoroethane | 353,15 | 3,23 | Cyclohexane | 553,5 | 4,07 |
| Hydrogen bromide | 363,15 | 8,55 | Benzene | 562,2 | 4,89 |
| Propylene | 364,95 | 4,60 | Toluene | 591,8 | 4,10 |
| Chlorodifluoromethane | 369,3 | 4,97 | Water | 647,3 | 22,12 |

Table 1: Critical data of selected fluids, from A. Bertucco and G. Vetter, *High Pressure Process Technology: Fundamentals and Applications* vol. Industrial Chemistry Library, Volume 9: Elsevier, 2001.

Fig. 11

METHOD FOR PROCESSING COALESCENCE-INHIBITED EMULSIONS FROM WHOLE-CELL BIOTRANSFORMATIONS WITH COMPRESSED OR SUPERCRITICAL GASES

CROSS REFERENCE TO RELATED APPLICATIONS

This application is the National Stage of PCT/DE2008/001177 filed on Jul. 20, 2008, which claims priority under 35 U.S.C. §119 of German Application No. 10 2007 034 258.8 filed on Jul. 21, 2007 and German Application No. 10 2007 059 389.0 filed on Dec. 6, 2007. The international application under PCT article 21(2) was not published in English.

The invention relates to a method for processing coalescence-inhibited emulsions having components from whole-cell biotransformations, with compressed or supercritical gases, particularly with carbon dioxide.

An aqueous/organic two-phase system is often used for biocatalytical reaction of apolar organic molecules [1-5]. This system allows the use and the accumulation of high concentrations of poorly water-soluble substrates and products, whereby the organic phase, consisting of an apolar, non-toxic solvent or a mixture of multiple solvents serves as a substrate reservoir and/or as a product sink. Furthermore, the organic phase protects against toxic effects of substrates and products. Furthermore, the characteristic distribution of substrates and products in the two phases can be utilized to prevent kinetic product inhibition, to steer equilibrium reactions into the desired direction, to increase enantioselectivity, and to control multi-step reactions.

Typically, such two-phase systems are strongly emulsified, in order to achieve high mass transfer rates. The formation of stable emulsions is also promoted by high biocatalyst concentrations, especially if whole microbial cells are used. In this connection, high concentrations of macromolecular surfactant substances (lipids, proteins, polysaccharides, biosurfactants, cell fragments) occur [6-9].

Since solvent recycling is essential in two-phase bioprocesses, along with product isolation, for economical and ecological reasons, the two phases have to be separated from one another after the biotransformation. This phase separation has proven to be difficult in the case of stable coalescence-inhibited emulsions, as they occur when using whole microbial cells. Various methods for phase separation, such as centrifugation, membrane filtration, filter coalescence, addition of de-emulsifiers, or thermal methods, yielded unsatisfactory results or were very complicated in terms of apparatus or time-consuming [7]. Complicated phase separation is considered one of the main limitations for industrial implementation of two-phase bioprocesses, which have great economic and ecological potential. There is therefore a need for innovation in the field of phase separation in two-phase whole-cell biotransformations.

Typically, the systems from biotransformation are at first separated roughly by means of centrifugation. Subsequently, multiple filtration and (ultra)centrifugation steps are carried out, in order to achieve sufficient separation. The organic phase, which is obtained in this very complicated manner, is subsequently subjected to distillation or extractive processing, in order to separate out the valuable product. (However, sufficient phase separation cannot be achieved in this connection. Therefore, it is not possible to separate the organic phase that contains the valuable product completely from the aqueous phase, and this makes further processing significantly more difficult.)

In other separation methods, an attempt is made to purify the emulsion by distillation, after rough mechanical separation of other components, whereby problems occur in the column due to fouling and two-phase nature of the emulsion. In the case of an enzymatic method, the emulsion is separated with good results by means of the use of hydrolases. Except for the last method mentioned, none of the other prior methods are able to achieve defined phase separation. Complete separation of both the cell components and the aqueous phase from the organic phase has not been possible up to now. In this connection, separation of the cell mass is of great importance, since it can lead to encrusting or clogging in subsequent process steps. Using the alternative solution approaches described, no permanent separation of the phases can furthermore be achieved. Furthermore, a disadvantage of the prior methods, in addition to the large number of purification steps, is the use of a solvent that might be necessary for extraction, and subsequently has to be recovered.

The separation of aqueous/organic two-phase systems that is being discussed here will be described in the following, using the example of separation of coalescence-inhibited emulsions from two-phase whole-cell biotransformations, for example in apolar solvents. The reaction mixture that is present in this connection, after the biotransformation has taken place, does not separate spontaneously and is present essentially as shown in FIG. 1 after standing for an extended period of time. The mixture optically consists of three phases, whereby a milky organic/aqueous emulsion forms the top phase (I), which contains not only the organic solvent but also the educt, by-products, and the product. Furthermore, this emulsion also contains dissolved components and surfactant substances (salts, nutrients, lipids, proteins, polysaccharides, biosurfactants). The second phase (II) that can be optically identified is an aqueous phase, in which the nutrients necessary for cultivation (some of which are also still present in the emulsion) are found, and from which the cells/biomass (III) settle in a third phase.

The complexity of the present reaction mixture becomes even clearer if one attempts to separate the two-phase system by means of conventional methods such as centrifugation. Thus, the appearance shown in FIG. 2 is obtained even after extended centrifugation. After longer centrifugation of the mixture from FIG. 1, the influence of the macromolecular surfactant substances (lipids, proteins, polysaccharides, biosurfactants, cell fragments) present in the emulsion can be clearly seen. While cells contained in the aqueous phase settle at the bottom of the vessel (IV), and the aqueous phase (III) demonstrates a sharp upper phase boundary, only insufficient separation into an organic phase (I) and an interphase or emulsion phase (II) can be observed in the emulsion (phase I in FIG. 1).

Different application cases are known in which gasification of an emulsion of oil and water by means of $CO_2$ was used for separating the two components oil and water. For example, such a method is known from DE 40 28 904 C1 or DE 197 54 756 C1 in each instance, with which so-called lubricants for cooling mechanical machining processes are processed after use, in this manner. However, such emulsions are very easy to separate, since they are relatively unstable simple emulsions composed of two substances that act quite differently, and generally no components of a biochemical nature that stabilize the emulsion are contained in them.

In petrochemical processes, as well, "oil in water" emulsions frequently occur [10, 11], which are also known from U.S. Pat. No. 6,566,410 B1, for example. Similar areas of use are known from DE 101 14 920 A1, for example, for extraction of organic monomers.

Furthermore, methods are known in which extractions of biomaterials that are present in single-phase substance mixtures (and have contaminants) are undertaken by means of carbon dioxide. In such methods, however, the carbon dioxide serves as a carrier of chemical substances that perform the corresponding extraction, and these methods can therefore not be compared with de-mixing of multi-phase substance mixtures.

It is therefore the task of the present invention to indicate a method with which the components of coalescence-inhibited emulsions from whole-cell biotransformations can be separated from one another, in such a manner that clean separation, productive with regard to amount throughput, can be carried out in a short period of time.

The solution for this task results from the method described below. Further advantageous embodiments of the invention are also described herein.

The invention proceeds from a method for processing a coalescence-inhibited emulsion having components from whole-cell biotransformations, such as cells, soluble cell components, organic solvents and/or water. In this connection, in the manner according to the invention, such a method is developed further in that the coalescence-inhibited emulsion, which is stable after biotransformation, is combined, in a container, with at least one compressed or supercritical gas, in excess, and mixed with it for a period of time that can be predetermined, at elevated pressure and elevated temperatures, after which time the aqueous and the organic phase of the emulsion separate from one another, and the cells and cell components of both the aqueous and the organic phase precipitate in the region of their boundary surfaces or phase boundary surfaces, and are subsequently separated. After addition of the compressed or supercritical gas, such as carbon dioxide, preferably in excess (e.g. of about 3 parts by mass of compressed carbon dioxide per part by mass of emulsion) and preferably at a pressure of about 115 bar, for example, and at a temperature of about 45° C., for example, the emulsion is intensively mixed with the compressed or supercritical gas for preferably 2 minutes. The higher the temperature used is selected to be here, the higher the pressure should also be selected to be. After the mixer is shut off, a sharp separation between the aqueous and the organic phase can subsequently be observed, whereby cell components precipitate at the boundary surfaces of the phases (also at a boundary surface with a container or the like), at the lower end of both the aqueous phase and the organic phase. These cell components can now be separated in simple manner, since in contrast to the original emulsion, they sediment more rapidly. Even after pressure relaxation, the phases separate from one another rapidly even after being mixed together repeatedly. The organic phase, which contains the valuable product, can then be processed efficiently, for example by means of supercritical extraction. In this connection, the method according to the invention offers tremendous potential for separating emulsions from biocatalytical processes (such as whole-cell biotransformations using microorganisms as catalysts, for example) and for processing them with little apparatus expenditure and in cost-advantageous manner. In this connection, high efficiency in other method steps can also be achieved by means of the use of compressed or supercritical gases, such as compressed carbon dioxide, for example, as the solvent. In this connection, the effect of the compressed or supercritical gas, such as the carbon dioxide, for example, is probably primarily based on a purely physical interaction with the components of the emulsion, which leads to targeted de-mixing of the phases (and components) of the emulsion and thus makes the mixture of the phases (and components), which is otherwise very difficult to separate, separable in the first place, in technical practical manner. The method proposed here for processing of emulsions from whole-cell biotransformations with compressed or supercritical gases, such as compressed carbon dioxide, for example, yields a significant improvement in the purification of the reaction mixtures described, as a result. After only brief mixing (2 min) of the emulsion with the compressed or supercritical gas, the phase behavior shown in FIG. 3 occurs. After carbon dioxide, for example, has been compressed into the reaction mixture, not only can it be seen that the cells (IV) found in the aqueous phase (III) are settling at the bottom of the vessel, but also that the cell fragments/macromolecules (II) found in the interphase/emulsion phase are collecting at the phase boundary surface between an organic phase (I) and an aqueous phase (III). This happens within a very short time (typically less than 2 minutes) after the stirrer is shut off. In this connection, it is advantageous if the volume ratio of organic to aqueous phase is 1:1. The separation state obtained by means of the processing with compressed or supercritical gas such as compressed carbon dioxide, for example, is maintained even after relaxation and de-gassing of the compressed or supercritical gas (and renewed mixing), so that subsequent separation can take place both at atmospheric pressure and under elevated pressure. For reasons of energy efficiency, however, it can be practical here to prefer further separation under elevated pressure. This is primarily due to the fact that aside from conventional separation methods for purification of the valuable product from the organic phase, extraction with compressed carbon dioxide is also a possibility.

By means of the use of compressed or supercritical gases, the result can furthermore be achieved that as a function of the composition and properties of the emulsion, a suitable compressed or supercritical gas or even a plurality of such gases are simultaneously introduced into the emulsion, in order to thereby allow separation of the emulsion into the different phases. Therefore, the method can fundamentally be carried out with all compressed or supercritical gases, whereby implementation with carbon dioxide is particularly advantageous. To the extent that in the description of the method that follows, the compressed or supercritical gas is spoken of as being carbon dioxide, this should always be considered to be an abbreviation, as an example, for the term compressed or supercritical gas, and to be interpreted in the sense that aside from or as an alternative to the carbon dioxide explicitly mentioned, other compressed or supercritical gases, whether individually or as mixtures, can also be used according to the information provided here.

It is furthermore advantageous if a gas whose critical data are similar to the critical data of carbon dioxide is used as the compressed or supercritical gas. Since the solubility of carbon dioxide in emulsions is particularly advantageous for separation of the emulsion, it can also be expected when using compressed or supercritical gases having similar critical data and/or solution properties that a corresponding separation of the phases of the emulsion can be brought about. In this connection, similarity of the critical data and/or solution properties is understood to mean that similar effects are brought about in the emulsion, as those that were also found for carbon dioxide. The gases indicated in FIG. 11 can be viewed as a non-restrictive listing of such suitable gases, which are used industrially for high-temperature processes and thus can fundamentally be suitable for the method described here, as well. It is explicitly pointed out that other compressed or supercritical gases can also be used. The use of gases other than carbon dioxide is particularly practical if the gas in question develops particular solution properties in an emulsion, as a function of the composition of this emulsion, and thus simplifies or improves separation.

It is particularly preferred if propane, butane, or similar gases are used as a compressed or supercritical gas. The critical data and solution properties of such low-valence hydrocarbons is quite similar to that of carbon dioxide, and thus suitable for implementation of the method according to the invention. Furthermore, such gases are available in cost-advantageous manner and are essentially non-problematical in terms of environmental technology.

It is also possible that a mixture of two or more compressed or supercritical gases is used in place of a single gas.

Furthermore, it is possible that when using a compressed or supercritical gas having poorer solution properties than carbon dioxide in the emulsion, the gas is introduced into the emulsion under elevated pressure and/or the emulsion is separated and thus the poor solution properties are least partly compensated.

It is particularly advantageous that the cells and cell components precipitate at the lower end of both the aqueous and the organic phase. In this way, targeted withdrawal of these components (phases and solids) of the emulsion can be achieved in simple manner, in terms of equipment technology, and corresponding entrainment of non-desired components into the individual fractions can be avoided. In particular, these separated phases can be subjected to further purification, particularly for obtaining a valuable substance contained in at least one of the phases. In this connection, any substance within the emulsion that represents an intended result of the biocatalytic process and is supposed to be made available for a corresponding use, in amounts that are usually subject to the technology, is considered to be a valuable substance.

Of course, it is also possible that the aqueous phase with the precipitated cells and cell components, as well as the organic phase with the precipitated cells and cell components, are drawn off from the de-mixed emulsion separately, and can be subjected to further purification, for example by means of sedimentation methods or the like, separately, in each instance, in order to obtain the cells or cell components.

In a first possible embodiment, the emulsion can be mixed with the compressed or supercritical gas, in a container, in so-called batch operation, whereupon the phases separate in the same container, after mixing, and form a layered arrangement of the individual phases or components in the container, after which the phases or components are drawn from the container separately, from the individual layers. In this way, only a single container is required for mixing the emulsion with the compressed or supercritical gas, and for separation of the individual fractions, thereby minimizing the apparatus technology expenditure.

For continuous separation, it is also possible, in another embodiment, that the emulsion is intensively mixed with the compressed or supercritical gas in a first container, and the homogeneous mixture of emulsion and compressed or supercritical gas produced in this way is transferred to a second container, in which the phases separate, preferably while stirring slowly, and form a layered arrangement of the individual phases or components in the second container, after which the phases or components are drawn from the individual layers separately, from the second container. However, this solution is problematic in terms of regulation technology, since the filling levels in the second container and thus the location of the phase boundary surfaces must be kept constant.

In another possible embodiment for eliminating this problem, the emulsion is intensively mixed with the compressed or supercritical gas in a first container, and the homogeneous mixture of emulsion and compressed or supercritical gas is transferred to a second container, in which the aqueous and the organic phase separate from one another, preferably while stirring slowly, after which the aqueous and the organic phase are separately drawn off from the second container into additional containers, in which the cells and cell components of the aqueous and the organic phase as well as the compressed or supercritical gas can then be separated. Thus, the stated problems of process control can be reduced or avoided.

It is furthermore possible that in this connection, an elevated pressure and an elevated temperature prevail in the first container, and that separation takes place under ambient conditions in the second container. Depending on the emulsion to be processed, however, it can certainly be practical if an elevated pressure and an elevated temperature prevail in both containers.

With regard to inclusion of the separation according to the method described above into a total sequence for obtaining the individual fractions of the emulsion, it can be practical if direct processing of the emulsion to obtain a valuable substance takes place after biotransformation and before separation of the emulsion into the individual phases. In this way, early separation of the valuable substance can be brought about, thereby taking place in a manner that is gentle on the material, and afterwards, simple separation of the solid components of the emulsion or recycling of the solvent can take place.

It is possible, in this connection, that processing includes an extraction step for obtaining a valuable substance, preferably from the organic phase of the emulsion. Such extractions, also using supercritical carbon dioxide, for example, as a compressed or supercritical gas, are fundamentally known and serve, for example, in many cases, for obtaining individual substances from plant components such as in spice collection. In this connection, in a further embodiment, the valuable substance can be separated out of the emulsion directly and can be drawn off separately and/or together with contaminants. It is practical, in this connection, if only the extracted valuable substance and the organic solvents as well as compressed or supercritical gas are separated out of the emulsion and drawn off separately, in order to bring about complete separation of the valuable substance, with recovery of solvent and compressed or supercritical gas, in a targeted processing step.

It is furthermore advantageous if the remaining emulsion is further separated in a separation step that follows the direct extraction of the valuable substance, with the addition of compressed or supercritical gas, and the components of the emulsion are drawn off separately. In this way, as well, substances that can be used again can be recovered in targeted manner.

It is particularly possible that separation of the valuable substance and compressed or supercritical gas is carried out by means of rapid pressure reduction of the components separated out of the emulsion. In this way, the compressed or supercritical gas gasses out of the mixture with the valuable substance, and can be recovered in very pure form and in energetically simple manner.

It is also possible that after separation of the emulsion by means of compressed or supercritical gas, such as carbon dioxide, for example, processing only of the phase with the cell components present in it takes place by means of a separation method in which the valuable substance and/or compressed or supercritical gas are separated from the solvent.

For example, extraction by means of compressed or supercritical gas can be carried out as a separation method. For this purpose, the compressed or supercritical gas already used for the cell/emulsion separation can also be used for extraction. This gas can easily be recovered after extraction has taken place, by reducing the pressure, and can be reused in the process.

Alternatively to processing methods that contain extraction, at least one method step from among chromatography, crystallization, distillation, adsorption, absorption, membrane methods or filtration, or combinations of these methods, can also be used as a separation method for separating the valuable substance from an organic phase without biogenic components.

FIG. 10 shows extraction behavior of the emulsion for a sample solution.

FIG. 11 shows a table containing critical data of selected fluids that are used industrially for use in high-pressure method processes and can also be used in the method according to the invention.

In FIGS. 4 to 10, various process sequences are shown, with which an emulsion formed from a biotransformation can be separated into its individual components, whereby this method is also particularly suitable for use on a large technical scale.

DETAILED DESCRIPTION OF THE PREFERRED EMBODIMENTS

Figure 3:
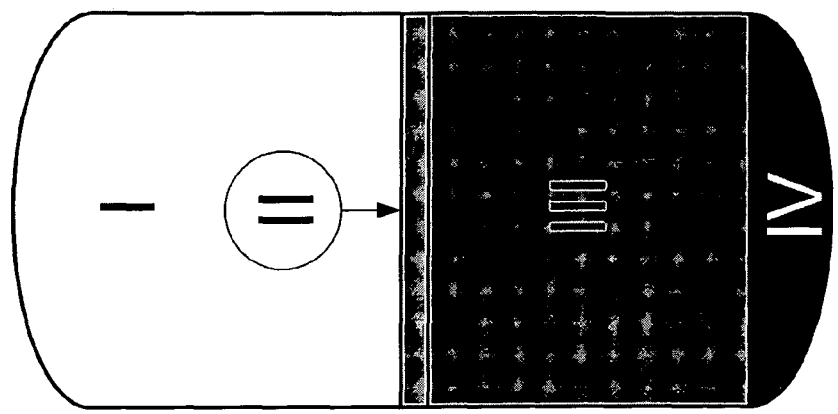
FIG. 3 shows typical positioning of the phases in a reaction mixture after application of the method according to the invention.
Figure 1:
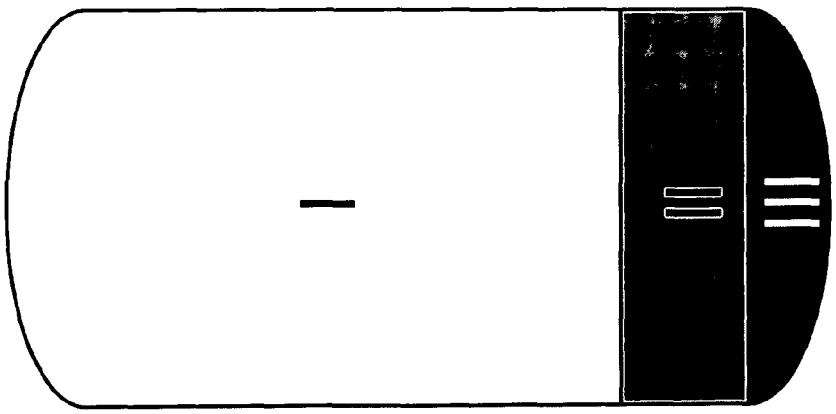
FIG. 1 shows typical positioning of the phases in a reaction mixture after biotransformation and after settling.

In the method presented, the cell suspension from a biotransformation (phases I, II, and III from FIG. 1) is directly placed into a pressurized container (FIG. 6) and tempered to approximately 45° C. Subsequently, compressed or supercritical gas, such as carbon dioxide, for example, is metered into the emulsion, using a suitable device, until the carbon dioxide proportion with reference to the total mass amounts to about 75%. The pressure of the mixture is increased to about 115-120 bar, and the mixture is intensively mixed for at least two minutes. After the stirrer is shut off, the desired phase separation and cell separation occurs in the pressurized container, as shown schematically in FIG. 3. In this connection, phase IV represents an amount of cells separated off from the aqueous phase III. Subsequently, the system obtained can be subjected to simple separation in one or two settler units and/or the organic phase can be passed directly to a subsequent supercritical extraction with carbon dioxide, in order to obtain the actual valuable product from this phase.

Figure 2:
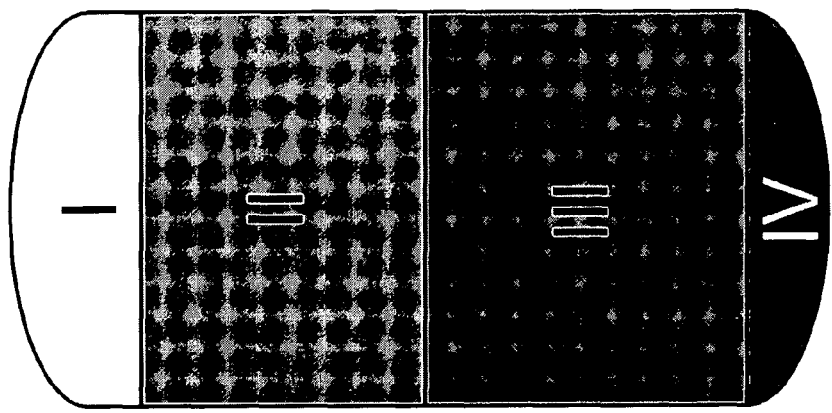
FIG. 2 shows typical positioning of the phases in a reaction mixture according to FIG. 1 after extended centrifugation.

It was possible to observe that the phase separation is maintained even after the carbon dioxide is drained off. Thus, a significantly improved and faster phase separation can be observed subsequently, even at atmospheric pressure and room temperature. The cell components (phase I in FIG. 1 and phase II in FIG. 2) that were previously contained in the emulsion are now situated at the phase boundary surface between the aqueous phase (phase II in FIG. 1 and phase III in FIG. 2) and the organic phase (phase I in FIG. 2 and FIG. 3) and can easily be separated off (phase II and, for the cells, phase IV in FIG. 3).

Studies of the interphases between the organic phase and the aqueous phase have shown that a change can be found. Thus, it can already be seen at 100× magnification under the microscope that agglomeration of the cell components at the phase boundary surface takes place in the emulsion before the treatment with carbon dioxide. After the treatment with compressed carbon dioxide, this can no longer be seen under the microscope at the same magnification. In contrast, sharp phase boundary surfaces are present, whereby the presumable cell components are present homogeneously in the lower region of the organic phase I.

By means of using compressed carbon dioxide, extraction of the valuable substance can be carried out after separation of the emulsion, insofar as the valuable substance dissolves in carbon dioxide under the given conditions.

Processing of the emulsion as described, with compressed or supercritical gases such as carbon dioxide, for example, can take place in one or in multiple steps. Possible variants of this are outlined in FIGS. 4 to 6.

Figure 4:
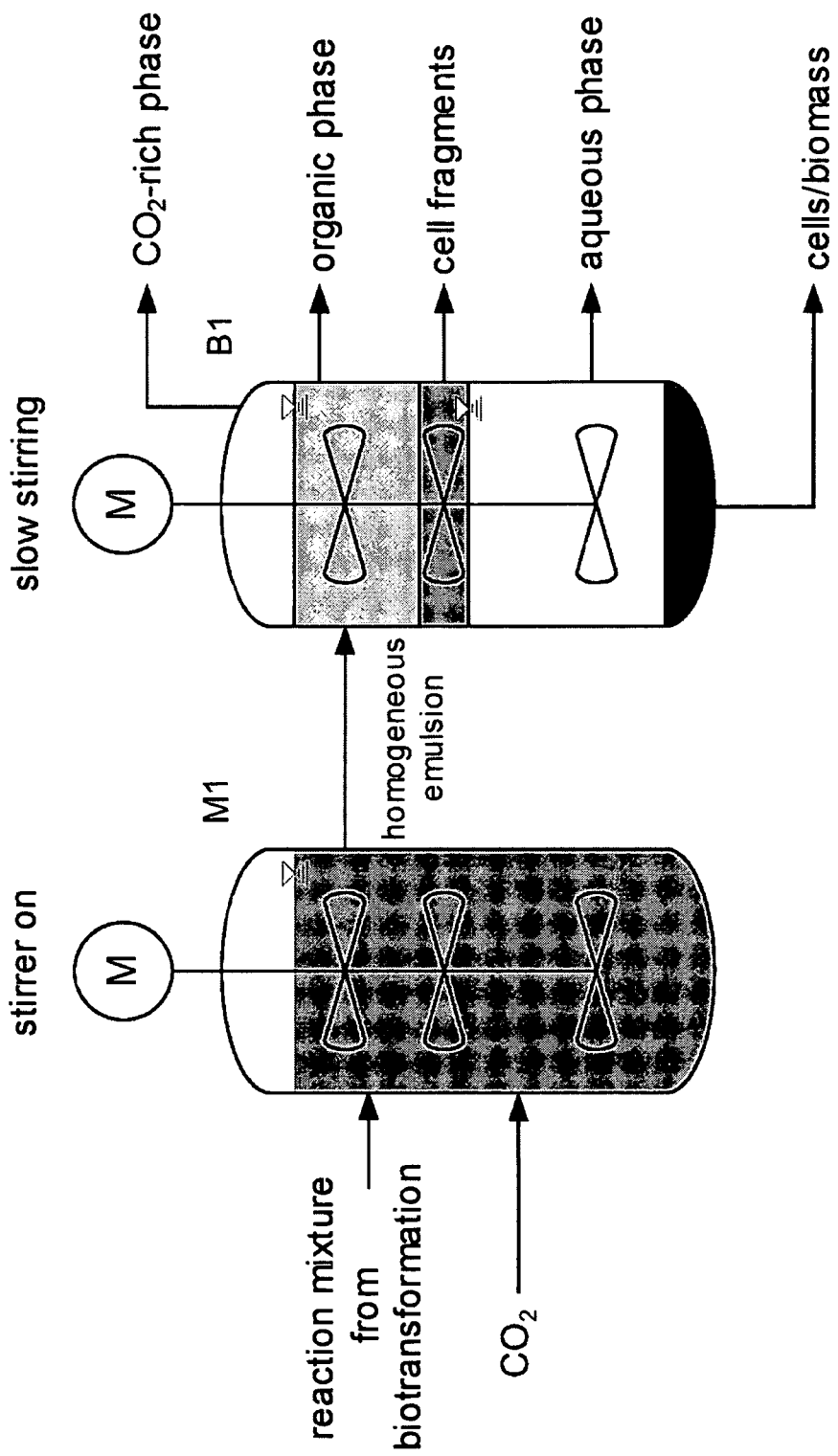
FIG. 4 shows a first preferred embodiment of a device for implementing the method according to the invention for separating the coalescence-inhibited emulsion.
Figure 5:
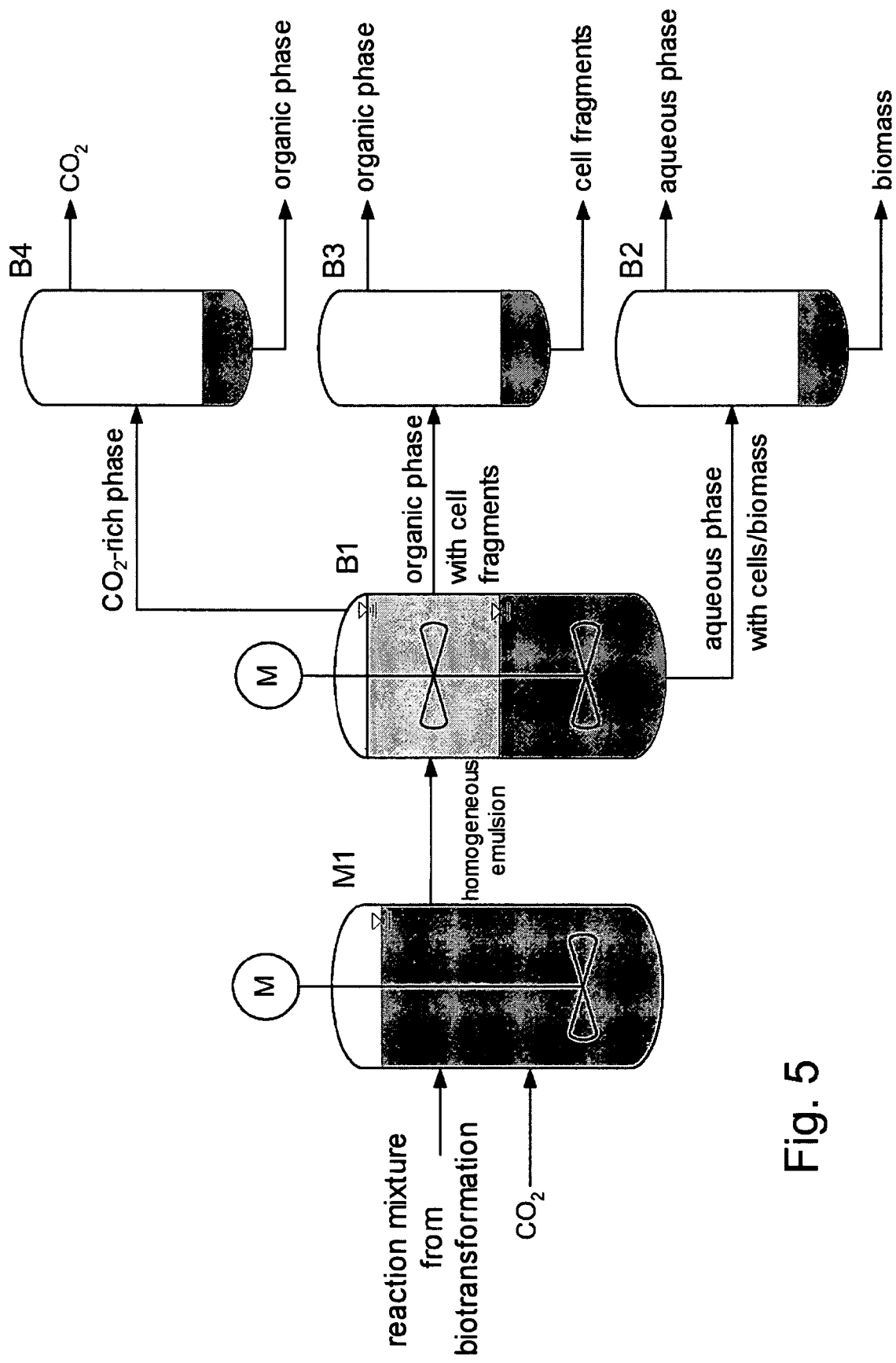
FIG. 5 shows another preferred embodiment of a device for implementing the method according to the invention for separating the coalescence-inhibited emulsion, in two steps.
Figure 6:
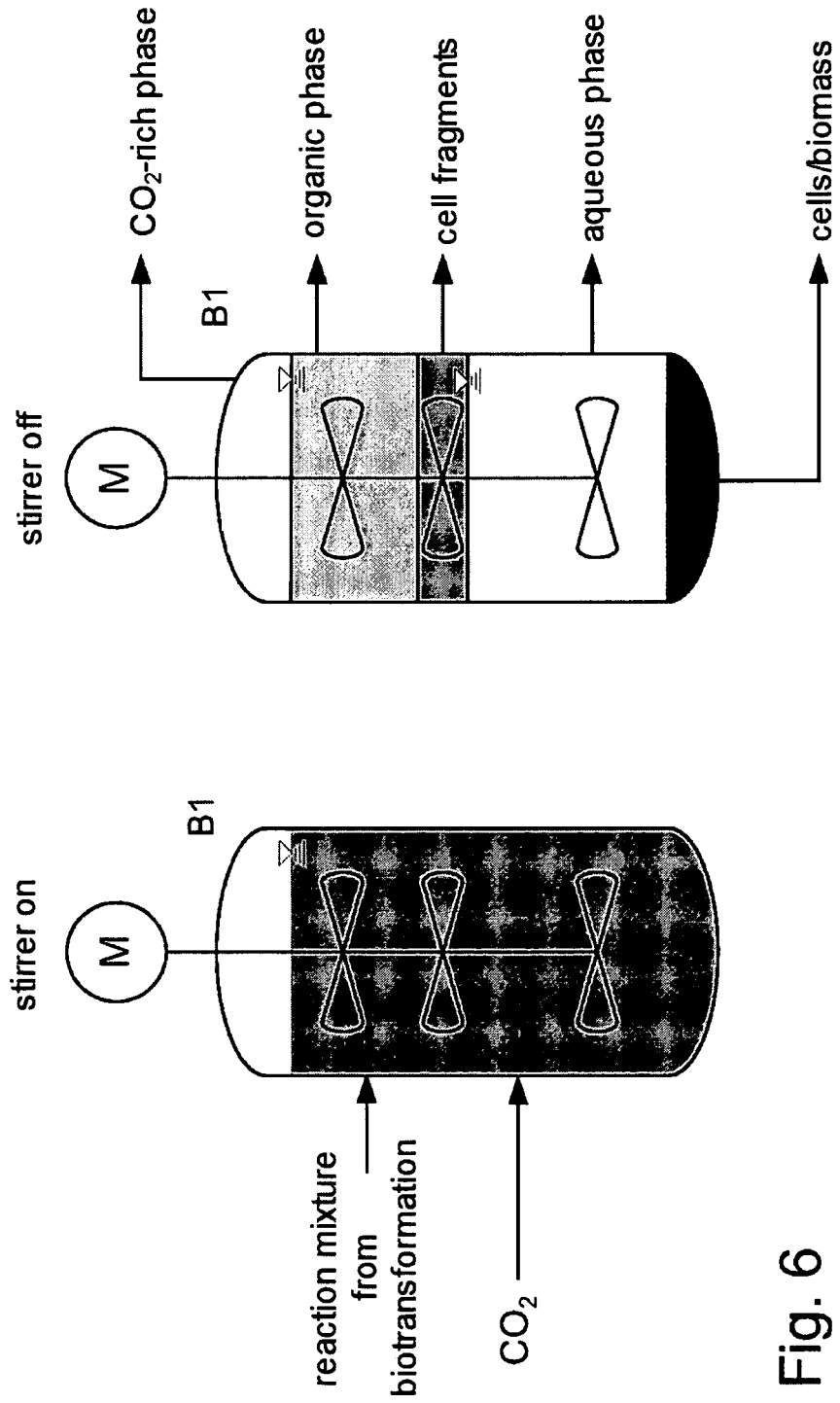
FIG. 6 shows another preferred embodiment of a device for implementing the method according to the invention for separating the coalescence-inhibited emulsion.

Separation of the coalescence-inhibited emulsion by means of a mixer/settler unit, as shown in FIG. 4, is problematic in terms of regulation technology, since the filling levels and thus the location of the phase boundary surfaces must be kept constant, but it makes do with few containers. For this purpose, the reaction mixture, together with carbon dioxide, is placed into a pressurized container M1 at elevated pressure and elevated temperature, and intensively mixed there. Subsequently, the homogeneous emulsion is placed into container B1, where phase separation occurs while stirring slowly with the motor-operated mixer M. The phases, in each instance, can be drawn off directly afterwards, in order to subject them to further purification.

Simpler regulation can be implemented if one divides the phase separation once again after the mixer M, and at first separates only the organic phase with cell fragments/macromolecules from the aqueous phase with cells/biomass. Subsequently, the solid components are then precipitated from the phases, in each instance, by means of sedimentation. This method is outlined in FIG. 5. Here, the reaction mixture is placed into a pressurized container M1 together with carbon dioxide, under elevated pressure and elevated temperature, and intensively mixed there. Subsequently, the homogeneous emulsion is placed into container B1, where phase separation between the organic phase with cell fragments/macromolecules and the aqueous phase with cells/biomass occurs, while stirring continues. The phases, in each instance, can afterwards be transferred to the containers B2-B4. Now, the solids are separated in the containers B3 and B4, by means of sedimentation.

Aside from continuous operation in a mixer/settler unit, batch operation in a single container is also possible, in this connection, in which container the reaction mixture is first mixed for a certain period of time, while metering in compressed carbon dioxide, and after the stirrer/homogenizer M is shut off, one waits for gravimetric separation. Here again, the phases, in each instance, can afterwards be drawn off directly (see FIG. 6). The reaction mixture, together with carbon dioxide, is placed into a pressurized container under elevated pressure and elevated temperature, and intensively mixed for a specific period of time. Subsequently, the stirrer/homogenizer M is shut off/slowed down, so that phase separation occurs. The phases, in each instance, can afterwards be drawn off directly, in order to subject them to further purification.

It is now possible to proceed further with the pure fractions obtained by means of one of the three variants.

Figure 8:
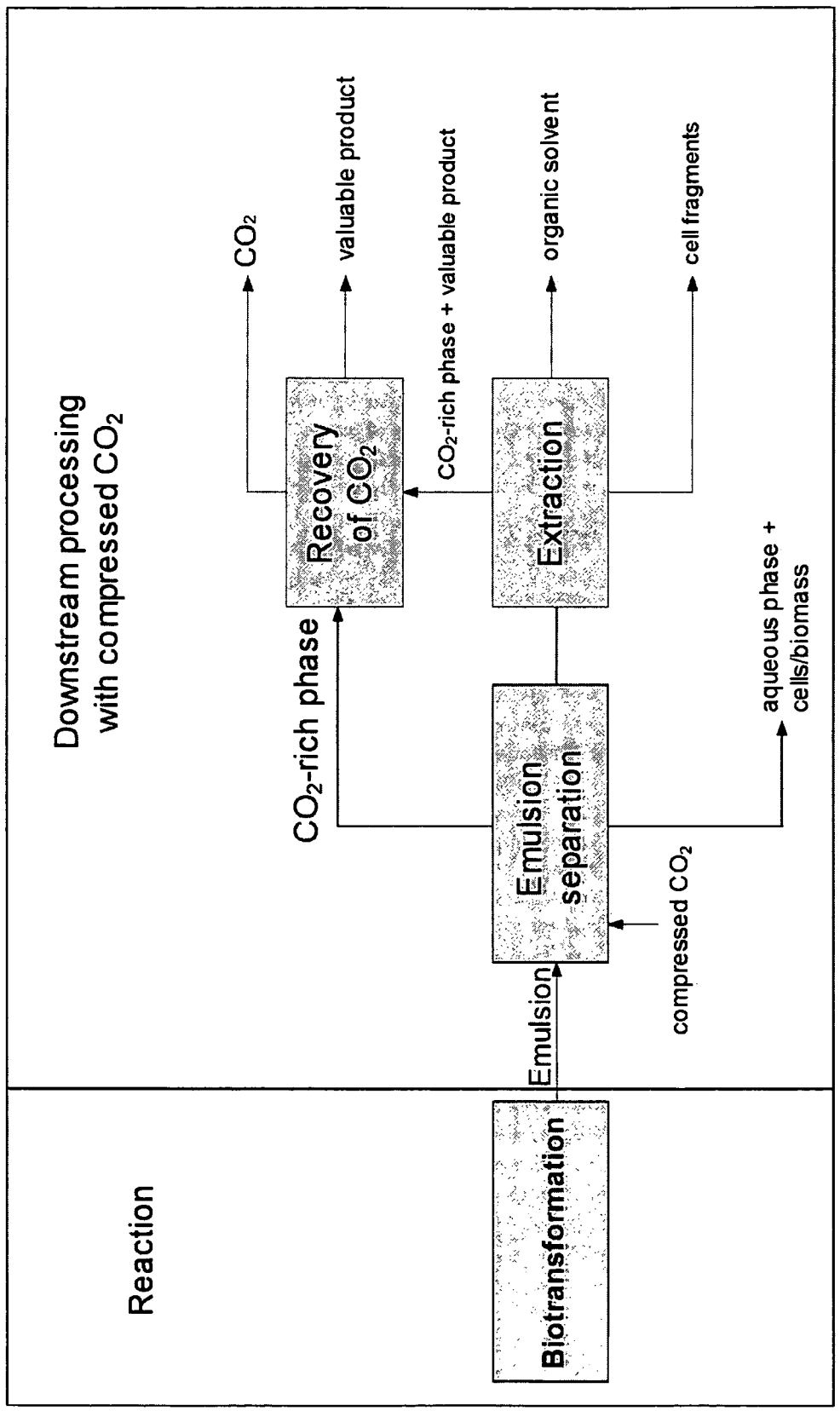
FIG. 8 shows another possibility for implementing the product processing by means of emulsion separation before extraction of the valuable product.
Figure 9:
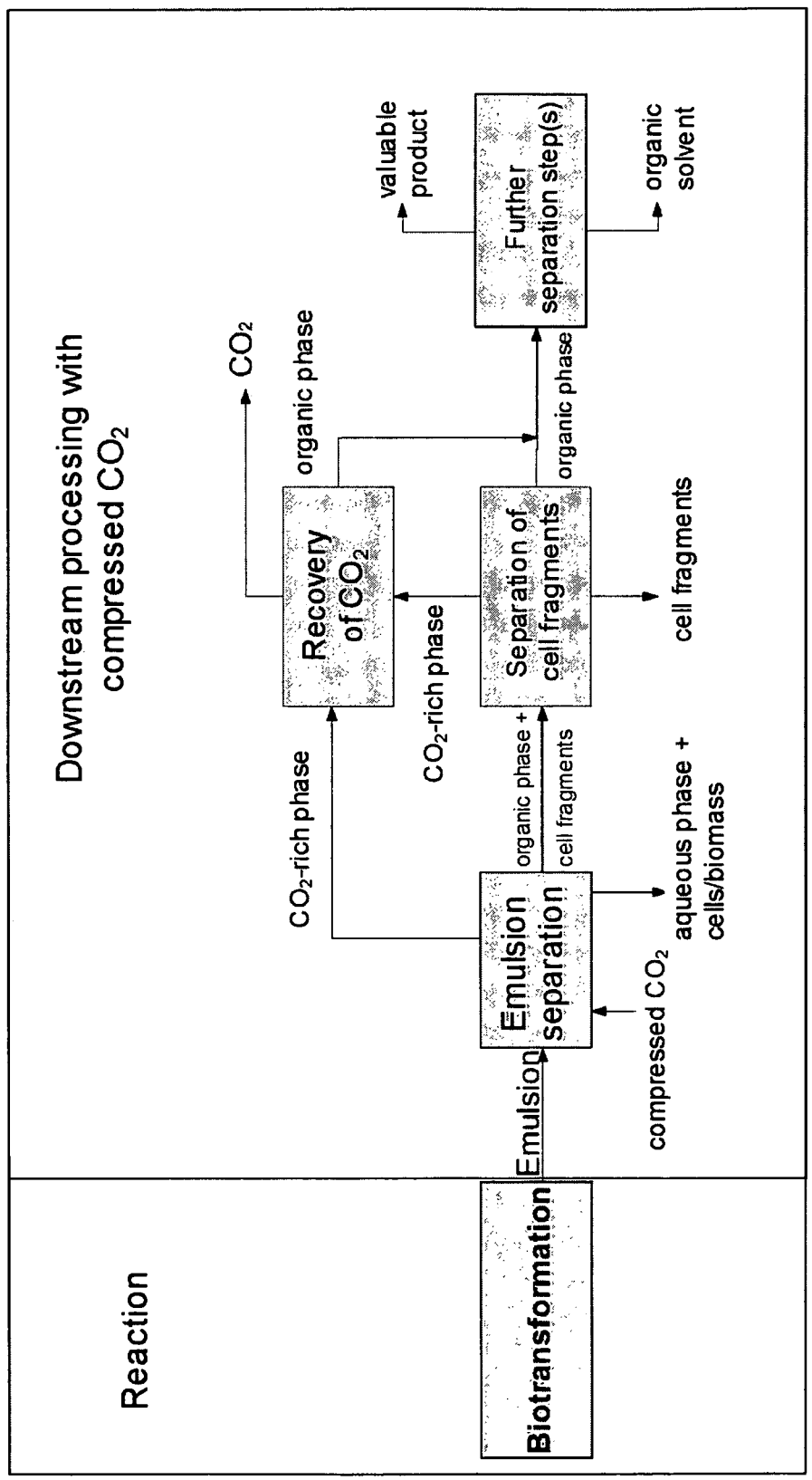
FIG. 9 shows another possibility for implementing the product processing by means of emulsion separation before isolation of the valuable product by means of a/multiple further separation step(s).

For the total process of obtaining the valuable substance, while simultaneously recovering the process substances as completely as possible, it can be practical to carry out separation of the emulsion before or after further processing, for example extraction, of the valuable product. Alternatives for carrying out product processing, proceeding from biotransformation, all the way to the pure valuable product, are shown in FIGS. 7 to 9.

Figure 7:
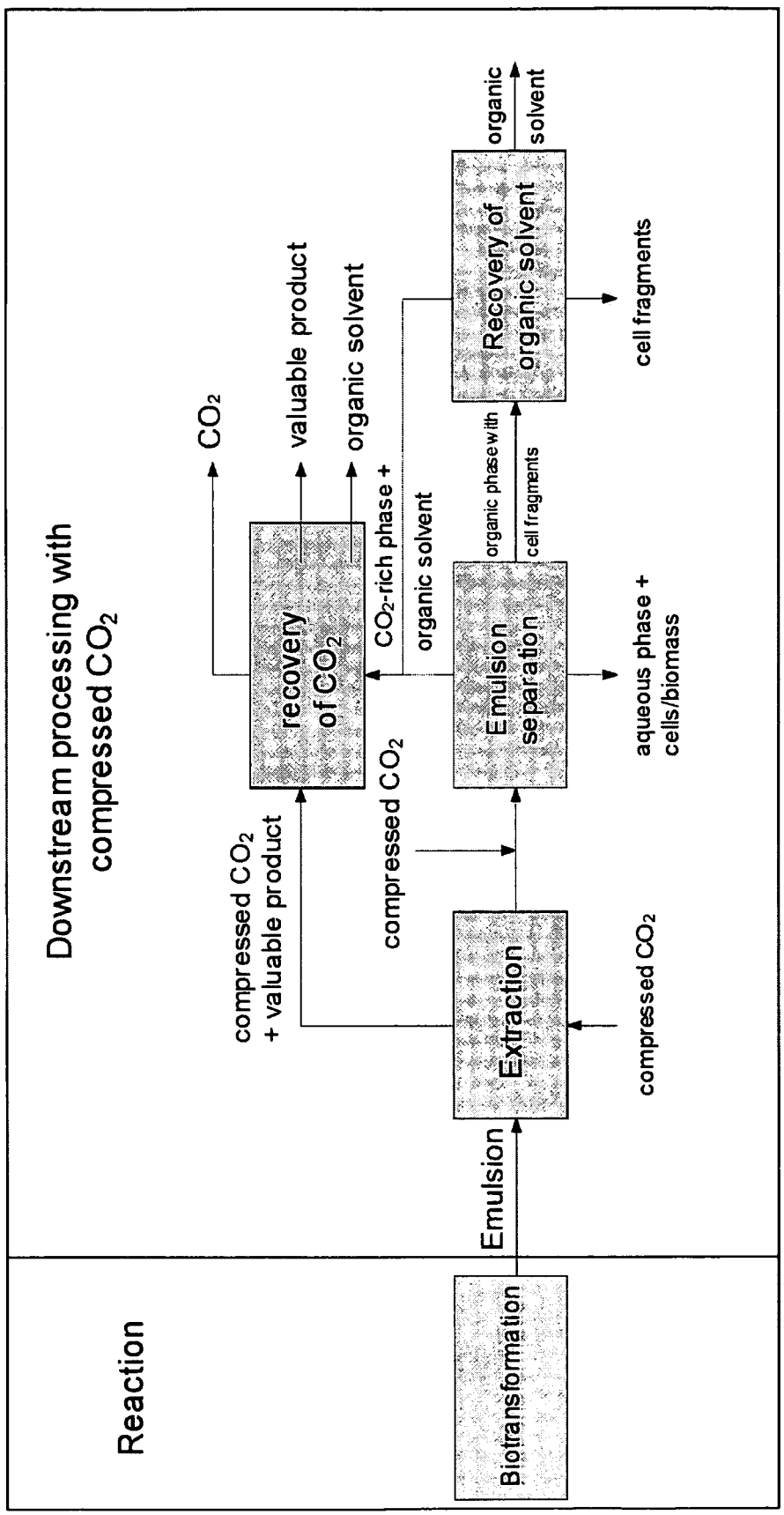
FIG. 7 shows a first possibility for implementing the product processing by means of emulsion separation after extraction of the valuable product has taken place.

In this connection, the method shown in FIG. 7 offers the advantage that the valuable product can be extracted directly from the emulsion. Proceeding from the biotransformation, the emulsion is directly transferred to extraction. Here, the valuable product is extracted directly, for example by means of compressed carbon dioxide, under elevated pressure and elevated temperature. By means of reducing the pressure, the valuable product precipitates and the carbon dioxide can be recycled. The remaining emulsion is subjected to phase separation as described, with compressed carbon dioxide, thereby making it possible to perform simple separation of the solid components as well as recycling of the solvent in further steps.

However, the mass stream passed to extraction is large. Prior separation of the aqueous phase, in which practically no valuable product at all is typically found, this mass stream can be significantly reduced, and this can lead to more efficient processing, as shown in FIG. 8. Proceeding from the biotransformation, the emulsion is subjected to phase separation as described, whereby the aqueous phase with cells/biomass is separated off. The remaining organic phase is subjected to a further purification step (e.g. extraction with compressed $CO_2$), in which the solids contained in the organic phase are separated off by means of sedimentation.

Alternatively to processing methods that contain extraction, other separation methods or any desired combinations of them are also possible for isolation of the valuable product, insofar as the organic phase is present free of biological substances after phase separation with compressed carbon dioxide. The most varied methods are suitable for this, such as chromatography, crystallization, distillation, adsorption, absorption, membrane methods, and filtration. In general, this variant is shown in FIG. 9. Proceeding from the biotransformation, the emulsion is subjected to the phase separation with compressed carbon dioxide as described, thereby separating off the aqueous phase with cells/biomass. The remaining organic phase is subjected to a further purification step, in which the solids contained in the organic phase are separated off by means of sedimentation. Subsequently, the pure organic phase obtained in this manner is subjected to a/multiple further separation step(s) to obtain the valuable product.

In FIG. 10, the extraction behavior of the emulsion when using the method according to the invention is shown as an example. The concentration, in the organic phase, of the substances indicated is plotted. It can be seen that the emulsion treated with 75 mass-% $CO_2$, in contrast to the original emulsion, has a significantly reduced concentration of the valuable substance styrene oxide.

A two-phase system after phase separation according to the method proposed above was considered as an example. This system consisted of an aqueous phase, as well as bis-2(ethylhexyl) phthalate as the main component of the organic phase, in which not only the valuable product styrene oxide but also octane, styrene, as well as 2-phenyl ethanol were present. Both phases were analyzed by means of gas chromatography before and after treatment with carbon dioxide. The concentration of the valuable substance styrene oxide in the organic phase decreased greatly as the result of the treatment with carbon dioxide; in the aqueous phase, styrene oxide could not be detected at all. Obviously, styrene oxide was extracted into the phase rich in carbon dioxide.

In FIG. 11, a table containing a listing of critical data of selected fluids can be seen, which fluids are used industrially for use in high-pressure method processes and can also be used in the method according to the invention. In this connection, this table is listed only as an example and does not restrict the use of other compressed or supercritical gases in the method according to the invention.

REFERENCES

[1] R. Leon, P. Fernandes, H. M. Pinheiro, and J. M. S. Cabral, "Whole-cell bio-catalysis in organic media," *Enzyme and Microbial Technology*, vol. 23, pp. 483-500, Dec. 15, 1998.

[2] M. D. Lilly, "Two-liquid-phase biocatalytic reactions," *Journal of Chemical Technology and Biotechnology*, vol. 32, pp. 162-169, 1982.

[3] P. Nikolova and O. P. Ward, "Whole cell biocatalysis in nonconventional media," *Journal of Industrial Microbiology*, vol. 12, pp. 76-86, February 1993.

[4] G. J. Salter and D. B. Kell, "Solvent selection for whole-cell biotransformations in organic media," *Critical Reviews in Biotechnology*, vol. 15, pp. 139-177, 1995.

[5] B. Bühler and A. Schmid, "Process implementation aspects for biocatalytic hydrocarbon oxyfunctionalization," *Journal of Biotechnology, vol.* 113, pp. 183-210, Sep. 30, 2004.

[6] H. M. Van Sonsbeek, H. H. Beeftink, and J. Tramper, "Two-liquid-phase bioreactors," *Enzyme and Microbial Technology*, vol. 15, pp. 722-729, September 1993.

[7] A. Kollmer, "Verfahrenstechnische Aspekte bei zweiphasigen Bioprozessen," in *Institute of Biotechnolgy* Zurich: Swiss Federal Institute of Technology, 1997, p. 202.

[8] R. G. Mathys, "Bioconversion in two-liquid phase systems: downstream processing," in *Institute of Biotechnolgy* Zurich: Swiss Federal Institute of Technology, 1997, p. 174.

[9] A. Schmid, "Two-liquid phase bioprocess development. Interfacial mass transfer reates and explosion safety," in *Institute of Biotechnolgy* Zurich: Swiss Federal Institute of Technology, 1997.

[10] S. D. Yeo and A. Akgerman, "Supercritical Extraction of Organic Mixtures from Aqueous-Solutions," *Aiche Journal*, vol. 36, pp. 1743-1747, November 1990.

[11] N. N. Zaki, R. G. Carbonell, and P. K. Kilpatrick, "A novel process for demulsification of water-in-crude oil emulsions by dense carbon dioxide," *Industrial & Engineering Chemistry Research*, vol. 42, pp. 6661-6672, Dec. 10, 2003.

The invention claimed is:

1. A method for processing an emulsion that is coalescence-inhibited comprising steps of:
    (a) carrying out a whole cell biotransformation in the presence of an organic solvent, water and whole cells of microorganisms as the catalyst, wherein an emulsion is directly produced by the whole cell biotransformation, the emulsion comprising the organic solvent, water, at least a portion of the whole cells and soluble cell components, wherein said emulsion is coalescence-inhibited and stable;

(b) placing the emulsion into a container with at least one compressed or supercritical gas that is in excess, and mixing the emulsion in the container with the at least one compressed or supercritical gas for a period of time that can be predetermined, at elevated pressure and elevated temperature compared to ambient pressure and temperature, respectively, (c) ending or reducing the mixing wherein an aqueous phase and an organic phase of the resultant mixed emulsion from step (b) separate from one another and whole cells and cell components of the aqueous phase precipitate in a region of a boundary surface of the aqueous phase, and whole cells and cell components of the organic phase precipitate in a region of a boundary surface of the organic phase, (d) subsequently separating the precipitated whole cells and cell components of the aqueous phase, the precipitated whole cells and cell components of the organic phase, the aqueous phase and the organic phase from one another; and (e) processing the resultant separated organic phase wherein a valuable substance contained in the separated organic phase is obtained.

2. The method according to claim 1, wherein the at least one compressed or supercritical gas comprises carbon dioxide.

3. The method according to claim 2, wherein the carbon dioxide is present in the container with the emulsion in an amount of two parts by mass of the carbon dioxide per part by mass of the emulsion.

4. The method according to claim 1, wherein the at least one compressed or supercritical gas has a critical temperature greater than or equal to 5.19 K and less than or equal to 647.3 K.

5. The method according to claim 1, wherein the at least one compressed or supercritical gas has a critical pressure greater than or equal to 0.23 Mpa and less than or equal to 22.12 Mpa.

6. The method according to claim 1, wherein the at least one compressed or supercritical gas comprises at least one of propane and butane.

7. The method according to claim 1, wherein the at least one compressed or supercritical gas comprises a mixture of two or more compressed or supercritical gases.

8. The method according to claim 1, wherein the ending or the reducing of the mixing occurs under elevated pressure.

9. The method according to claim 1, wherein the whole cells and cell components of the aqueous phase precipitate at a lower end of the aqueous phase, and
wherein the whole cells and cell components of the organic phase precipitate at a lower end of the organic phase.

10. The method according to claim 9, wherein the subsequent separation of step (d) occurs by separately drawing off the precipitated whole cells and cell components from each of the aqueous and organic phases wherein the resultant separated organic and aqueous phases are liquid phases, and wherein the processing of the separated organic phase of step (e) occurs by purifying the separated organic phase to obtain the valuable substance.

11. The method according to claim 1, wherein the resultant separated cells and cell components from the organic phase from step (d) are then separated via sedimentation and/or centrifugation.

12. The method according to claim 1, wherein the mixing lasts for a period of time of at least 1 minute.

13. The method according to claim 1, wherein steps (b) and (c) occur in the same container and result in the formation in the container of a layered arrangement of:
the aqueous phase,
the organic phase,
the precipitated whole cells and cell components of the aqueous phase, and
the precipitated whole cells and cell components of the organic phase; and
wherein the subsequent separation of step (d) occurs
(i) by drawing off the precipitated whole cells or cell components of the organic phase from the container from a first individual layer of the layered arrangement, and drawing off the precipitated whole cells or cell components of the aqueous phase from the container from a second individual layer of the layered arrangement, the drawing off of the precipitated whole cells or cell components of the organic phase occurring separately from the drawing off of the precipitated whole cells or cell components of the aqueous phase; or
(ii) by drawing off the organic phase from the container from a layer of the layered arrangement, and drawing off the aqueous phase from the container from a layer of the layered arrangement, the drawing off of the organic phase from the container occurring separately from the drawing off of the aqueous phase from the container.

14. The method according to claim 1, wherein the container is a first container, wherein the mixing of step (b) produces a homogeneous mixture of the emulsion and the at least one compressed or supercritical gas, wherein after the mixing is ended or reduced, the homogenous mixture is transferred to a second container wherein the separation of the aqueous phase and the organic phase from the emulsion, the precipitation of the whole cells and cell components of the aqueous phase and the precipitation of the whole cells and cell components of the organic phase occur in the second container and result in the formation of a layered arrangement in the second container of:
the aqueous phase,
the organic phase,
the precipitated whole cells and cell components of the aqueous phase, and
the precipitated whole cells and cell components of the organic phase, and
wherein the subsequent separation of step (d) occurs
(i) by drawing off the precipitated whole cells or cell components of the organic phase from the second container from a first layer of the layered arrangement and drawing off the precipitated whole cells or cell components of the aqueous phase from the second container from a second layer of the layered arrangement, the drawing off of the precipitated whole cells or cell components of the organic phase occurring separately from the drawing off of the precipitated whole cells or cell components of the aqueous phase; or
(ii) by drawing off the organic phase from the second container from a layer of the layered arrangement, and drawing off the aqueous phase from the second container from a layer of the layered arrangement, the drawing off of the organic phase from the second container occurring separately from the drawing off of the aqueous phase from the second container.

15. The method according to claim 14, wherein each of the separations and the precipitations in the second container take place under ambient conditions.

16. The method according to claim 14, wherein an elevated pressure and an elevated temperature prevail in the second container during each of the separations and the precipitations.

17. The method according to claim 1, wherein the separation step (d) occurs by drawing off the organic phase and the precipitated whole cells and cell components of the organic phase, and drawing off the aqueous phase and the precipitated whole cells and cell components of the aqueous phase, wherein the drawing off of the aqueous phase occurs separately from the drawing off of the organic phase.

18. The method according to claim 1, further comprising a step (f) of recovering the compressed or supercritical gas.

19. The method according to claim 1, wherein the processing of step (e) of the resultant separated organic phase to obtain the valuable substance comprises at least one member selected from the group consisting of a chromatography step, crystallization, distillation, adsorption, absorption, a membrane method, and filtration.

20. A method for processing of an emulsion that is coalescence-inhibited comprising steps of:
 (a) carrying out a whole cell biotransformation in the presence of an organic solvent, water and whole cells of microorganisms as the catalyst, wherein an emulsion is directly produced by the whole cell biotransformation, the emulsion comprising the organic solvent, water, at least a portion of the whole cells and soluble cell components, wherein said emulsion is coalescence-inhibited and stable;
 (b) placing the emulsion into a container with at least one compressed or supercritical gas that is in excess, and mixing the emulsion in the container with the at least one compressed or supercritical gas for a period of time that can be predetermined, at elevated pressure and elevated temperature compared to ambient pressure and temperature, respectively; and
 (c) ending or reducing the mixing step and isolating the valuable substance from the emulsion before a separation step of the emulsion.

21. The method according to claim 20, wherein the isolation of the valuable substance is by extraction of the emulsion.

22. A method for processing an emulsion that is coalescence-inhibited comprising steps of:
 (a) carrying out a whole cell biotransformation in the presence of an organic solvent, water and whole cells of microorganisms as the catalyst, wherein an emulsion is directly produced by the whole cell biotransformation, the emulsion comprising the organic solvent, water, at least a portion of the whole cells and soluble cell components, wherein said emulsion is coalescence-inhibited and stable;
 (b) placing the emulsion into a container with at least one compressed or supercritical gas that is in excess, and mixing the emulsion in the container with the at least one compressed or supercritical gas for a period of time that can be predetermined, at elevated pressure and elevated temperature compared to ambient pressure and temperature, respectively;
 (c) ending or reducing the mixing wherein an aqueous phase and an organic phase of the resultant mixed emulsion from step (b) separate from one another, whole cells and cell components of the aqueous phase precipitate in a region of a boundary surface of the aqueous phase, whole cells and cell components of the organic phase precipitate in a region of a boundary surface of the organic phase, and a supercritical phase is formed above the organic phase and above the aqueous phase, the supercritical phase containing a portion of the at least one supercritical or compressed gas and a first valuable substance of the emulsion;
 (d) drawing off the supercritical phase and further processing the drawn-off supercritical phase to obtain the first valuable substance;
 (e) subsequently separating the precipitated whole cells and cell components of the aqueous phase, the precipitated whole cells and cell components of the organic phase, the aqueous phase and the organic phase from one another; and
 (f) processing the resultant separated organic phase wherein a second valuable substance contained in the separated organic phase is obtained.

23. The method according to claim 22, wherein the further processing of the drawn-off supercritical phase in step (d) is carried out via pressure reduction to obtain the valuable substance from the supercritical phase.

* * * * *

UNITED STATES PATENT AND TRADEMARK OFFICE
CERTIFICATE OF CORRECTION

PATENT NO. : 8,431,358 B2  
APPLICATION NO. : 12/452769  
DATED : April 30, 2013  
INVENTOR(S) : Sadowski et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 313 days.

Signed and Sealed this
Eighth Day of September, 2015

Michelle K. Lee
*Director of the United States Patent and Trademark Office*